United States Patent [19]

Yokoyama et al.

[11] Patent Number: 4,518,354

[45] Date of Patent: * May 21, 1985

[54] SILVER HALIDE PHOTOGRAPHIC LIGHT-SENSITIVE MATERIALS WITH ANTISTATIC LAYER CONTAINING NONIONIC SURFACE ACTIVE AGENT

[75] Inventors: Shigeki Yokoyama; Akira Hibino; Yukio Maekawa; Hiroshi Kawasaki, all of Kanagawa, Japan

[73] Assignee: Fuji Photo Film Co., Ltd., Kanagawa, Japan

[*] Notice: The portion of the term of this patent subsequent to Apr. 9, 2002 has been disclaimed.

[21] Appl. No.: 497,285

[22] Filed: May 23, 1983

[30] Foreign Application Priority Data

May 21, 1982 [JP] Japan .................................. 57-85764

[51] Int. Cl.³ .................................................. G03C 1/78
[52] U.S. Cl. ..................................... 430/527; 430/631
[58] Field of Search ................................ 430/527, 631

[56] References Cited

U.S. PATENT DOCUMENTS

| | | | |
|---|---|---|---|
| 2,823,123 | 2/1958 | Knox et al. | 430/631 |
| 3,525,620 | 8/1970 | Nishio et al. | 430/631 |
| 3,850,641 | 11/1974 | Horigome et al. | 430/527 |
| 3,860,425 | 1/1975 | Ono et al. | 430/631 |
| 4,209,329 | 6/1980 | Lohner | 430/631 |
| 4,284,709 | 8/1981 | Tomka | 430/631 |

FOREIGN PATENT DOCUMENTS 861134 2/1961 United Kingdom .

Primary Examiner—Jack P. Brammer
Attorney, Agent, or Firm—Sughrue, Mion, Zinn, Macpeak & Seas

[57] ABSTRACT

A silver halide photographic light-sensitive material is disclosed. The photographic material is comprised of a support base, a silver halide emulsion layer and an antistatic layer. The antistatic layer contains a nonionic surface active agent having two polyoxyethylene chains in a molecule represented by the formula (I):

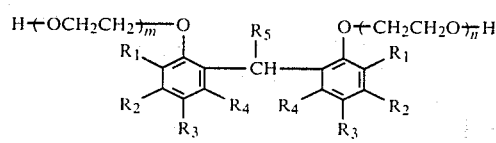

wherein $R_1$ and $R_3$ each represents a substituted or unsubstituted alkyl group, an aryl group, an alkoxy group, a halogen atom, an acyl group, an amido group, a sulfonamido group, a carbamoyl group or a sulfamoyl group, $R_2$ and $R_4$ each represents a hydrogen atom, a substituted or unsubstituted alkyl group, an aryl group, an alkoxy group, a halogen atom, an acyl group, an amido group, a sulfonamido group, a carbamoyl group or a sulfamoyl group, $R_5$ represents a hydrogen atom, a methyl group or an α-furyl group, and m and n independently represents an average degree of polymerization of ethylene oxide, which is 2 to 40. By utilizing the compound of general formula (I) it is possible to obtain a photographic material which aids in eliminating screen contamination. The compound has good antistatic properties which do not change with the passage of time. Furthermore, the compound does not have undesirable effects on the photographic properties of the photographic material.

8 Claims, No Drawings

SILVER HALIDE PHOTOGRAPHIC LIGHT-SENSITIVE MATERIALS WITH ANTISTATIC LAYER CONTAINING NONIONIC SURFACE ACTIVE AGENT

FIELD OF THE INVENTION

The present invention relates to silver halide photographic light-sensitive materials (hereinafter referred to as "photographic materials") and, particularly, to photographic materials having an improved antistatic property.

BACKGROUND OF THE INVENTION

Since photographic materials are generally composed of a base having an electrically insulating property and photographic layers, static charges are often accumulated when producing photographic materials or using them in such a way that they are subjected to contact friction between surfaces of the same or different kinds of material or separation thereof. The accumulated static charges cause various troubles. The most serious trouble is that the light-sensitive emulsion layer is exposed to light due to the discharge of accumulated static charges prior to development which causes dot spots or resinous or feathery linear spots upon development of the photographic film. This phenomenon results in what is referred to as a static mark. Due to the creation of such marks the commercial value of photographic films is remarkably damaged or, sometimes, completely lost. For example, it is easily understood that static marks can result in a dangerous judgment when they appear on medical or industrial X-ray films. Since this phenomenon first becomes evident after carrying out development, it is a very troublesome problem. Further, the accumulated static charges cause secondary troubles, for example, dusts adhere to the surface of films or uniform application cannot be carried out.

Such static charges are often accumulated when producing photographic materials or using them, as described above. For example, they may be generated during production by contact friction between the photographic film and a roll or by separation of the base face and the emulsion face during winding or rewinding the photographic film. Further, they are generated in an automatic photographing apparatus by contact of the X-ray film with machine parts or with fluorescent sensitizing paper or separation therefrom. In addition, they are generated in contact with packing materials, etc. Generation of the static marks induced by accumulation of such static charges becomes very substantial as there is an increase in the sensitivity of the photographic materials and an increase in the rate of processing. Particularly, in recent years, static marks are more easily generated, because the photographic materials have high sensitivity and there are many opportunities for the material to be subjected to severe handling such as high speed application, high speed photographing or high speed automatic processing, etc.

In order to remove troubles due to static electricity, it is preferred to add antistatic agents to the photographic materials. However, it is impossible to use antistatic agents conventionally used in other fields because there are various restrictions which are characteristic to photographic materials. For example, antistatic agents which can be utilized in photographic materials must have excellent antistatic properties and not have a bad influence upon photographic properties of photographic materials such as sensitivity, fogging, granularity or sharpness. Further, they must not have bad influences upon film strength (namely, scratches are not easily formed by friction or scratching). It is also important that they not have bad influences upon antiadhesive properties (namely, the surface of the photographic material does not easily adhere to the surface of another photographic material or other materials), that they not promote fatigue of processing solutions for the photographic materials, or that they not reduce adhesive strength between the layers of the photographic materials. Accordingly, the application of antistatic agents to photographic materials is subjected to many restrictions.

One method of removing problems created by static electricity comprises increasing the electrical conductivity of the surface of photographic materials so as to disperse static charges in a short time prior to discharge of accumulated charges.

Thus, methods of increasing the electrial conductivity of the base of photographic materials or various kinds of surface coating layer thereof have been proposed. An attempt has been made at utilizing various hygroscopic substances and water-soluble inorganic salts, certain kinds of surface active agents and polymers. For example, the use of polymers described in U.S. Pat. Nos. 2,882,157, 2,972,535, 3,062,785, 3,262,807, 3,514,291, 3,615,531, 3,753,716 and 3,938,999, etc., surface active agents described in U.S. Pat. Nos. 2,982,651, 3,428,456, 3,457,076, 3,454,625, 3,552,972 and 3,655,387, etc., and metal oxides and colloidal silica described in U.S. Pat. Nos. 3,062,700, 3,245,833 and 3,525,621, etc., are known.

However, it is very difficult to apply these substances to photographic materials, because they are specifically adopted to one kind of film base or one type photographic composition. Accordingly, they produce good results in connection with certain specified film base and photographic emulsion or other photographic elements, but they are useless in preventing static charges with different film bases and photographic elements. Alternatively, these substances may have excellent antistatic properties but have a bad influences upon photographic properties such as sensitivity of photographic emulsions, fogging, granularity or sharpness. In addition, some of these substances have an excellent antistatic properties just after production but these properties deteriorate with the passage of time.

Nonionic surface active agents having one polyoxyethylene chain in a molecule are described in British Pat. No. 861,134 and German Pat. No. 1,422,809 and these agents have an excellent antistatic properties. However, when they are applied to the photographic materials, there are various problems such as: (1) they remarkably deteriorate sensitivity, (2) since their antistatic properties deteriorate with the passage of time, though they have a good antistatic property just after production, the antistatic properties of products become inferior when they are used, and (3) when they are applied to X-ray sensitive materials, dotted or mesh-like uneven density (which is called "screen contamination") is formed on the X-ray sensitive materials after development, because the X-ray sensitive materials contact with sensitizing paper (screen) in case of photographing. Accordingly, the value of the products is remarkably reduced and, sometimes, it is completely lost.

On the other hand, U.S. Pat. No. 3,850,641 has disclosed a method in which an ethylene oxide addition polymer of phenol-formaldehyde resin is applied as the antistatic agent for the photographic materials. This polymer is synthesized by carrying out a condensation polymerization of phenol derivatives and formaldehyde to form the so-called phenol-formaldehyde resin, and thereafter carrying out addition polymerization of ethylene oxide.

The phenol-formaldehyde resin synthesized as described above is inevitably contaminated by unreacted phenol derivatives. Contamination of the unreacted phenol derivatives becomes more remarkable when synthesizing a resin having a lower degree of polymerization. Further, the process for removing unreacting phenol derivatives in the resin is remarkably troublesome, because of the resin. Even if removal operation is repeated, it is very difficult to completely remove the unreacted phenol derivatives. Accordingly, it is essentially impossible to industrially produce phenol-formaldehyde resin which does not contain any unreacted phenol derivatives.

In an ethylene oxide addition polymer of the phenol-formaldehyde resin contaminated with unreacted phenol derivatives, it is impossible to avoid various problems analogous to those in nonionic surface active agents having one polyoxyethylene chain in the molecule described in British Pat. No. 861,134 and German Pat. No. 1,422,803. These problems are unavoidable because the polymer will include some molecules having one polyoxyethylene chain in the molecule originated in the unreacted phenol derivatives in addition to molecules having many polyoxyethylene chains in the molecule.

Further, it is very difficult to obtain phenol-formaldehyde resin having a definite composition, because not only the content of unreacted phenol derivatives but also the average degree of polymerization on the distribution of degree of polymerization varies according to a slight variation of conditions for synthesizing the resin. In addition, it is easily understood that, when the ethylene oxide addition polymer of phenol-formaldehyde resin is produced by addition polymerization of ethylene oxide, it is remarkably difficult to control the polymer so as to have a definite composition to form an antistatic layer having a definite quality.

Moreover, other phenol resins such as phenol-acetaldehyde resin or phenol-furfural resin, etc., have similar problems.

SUMMARY OF THE INVENTION

A first object of the present invention is to provide antistatic photographic materials in which photographic properties are not badly affected, such as no desensitization, etc.

A second object of the present invention is to provide antistatic photographic materials which do not cause screen contamination.

A third object of the present invention is to provide antistatic photographic materials in which the antistatic property after production does not change with the passage of time.

A fourth object of the present invention is to provide antistatic photographic materials having stabilized quality in which the antistatic property hardly changes due to variations in the production conditions for the antistatic agent.

As a result of earnest studies relating to antistatic agents which do not contain compounds having one polyoxyethylene chain in the molecule which have a bad influence upon properties of photographic materials, the present inventors have found that photographic materials which have almost none of the bad influences of prior compounds can be obtained. These materials are surprisingly obtained when a surface active agent having two polyoxyethylene chains in the molecule represented by the following formula (I) is added to an antistatic layer in the photographic materials.

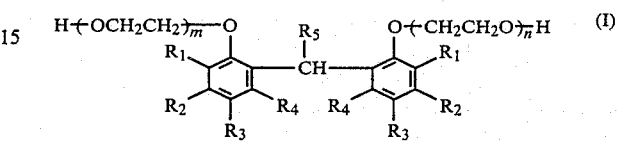

In the formula, $R_1$ and $R_3$ each represents a substituted or unsubstituted alkyl group, an aryl group, an alkoxy group, a halogen atom, an acyl group, an amido group, a sulfonamido group, a carbamoyl group or a sulfamoyl group, $R_2$ and $R_4$ each represents a hydrogen atom, a substituted or unsubstituted alkyl group, an aryl group, an alkoxy group, a halogen atom, an acyl group, an amido group, a sulfonamido group, a carbamoyl group or a sulfamoyl group, $R_5$ represents a hydrogen atom, a methyl group or an α-furyl group, m and n each represents an average degree of polymerization of ethylene oxide, which is 2 to 40 and m and n may be identical or different from each other.

DETAILED DESCRIPTION OF THE INVENTION

In the following, preferred embodiments of the present invention are illustrated.

$R_1$, $R_2$, $R_3$ and $R_4$ each represents a substituted or unsubstituted alkyl group having 1 to 20 carbon atoms such as a methyl group, an ethyl group, an i-propyl group, a t-butyl group, a t-amyl group, a t-hexyl group, a t-octyl group, a nonyl group, a decyl group, a dodecyl group, a trichloromethyl group, a tribromomethyl group, a 1-phenylethyl group or a 2-phenyl-2-propyl group, etc., a substituted or unsubstituted aryl group such as a phenyl group or a p-chlorophenyl group, etc., a substituted or unsubstituted alkoxy group represented by —$OR_6$ (wherein $R_6$ represents a substituted or unsubstituted alkyl group having 1 to 20 carbon atoms or an aryl group; the same meaning hereinafter), a halogen atom such as a chlorine atom or a bromine atom, etc., an acyl group represented by —$COR_6$, an amido group represented by —$NR_7COR_6$ (wherein $R_7$ represents a hydrogen atom or an alkyl group having 1 to 20 carbon atoms; the same meaning hereinafter), a sulfonamido group represented by —$NR_7SO_2R_6$, a carbamoyl group represented by

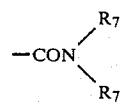

or a sulfamoyl group represented by

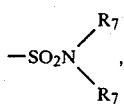

and $R_2$ and $R_4$ each may be a hydrogen atom. Among them, it is preferred that $R_1$ and $R_3$ each represents an alkyl group or a halogen atom. It is particularly preferred that $R_1$ represents a bulky tertiary alkyl group such as a t-butyl group, a t-amyl group or a t-octyl group, etc.

It is preferred that $R_2$ and $R_4$ each represents a hydrogen atom. Namely, compounds represented by the formula (I) synthesized from 2,4-di-substituted phenols are particularly preferred.

m and n each represents an average degree of polymerization of the polyethylene unit: $-(OCH_2CH_2)-$, which is 2 to 40 and, preferably, 5 to 30. m and n may be identical or may be different.

The compounds of the present invention can be prepared by carrying out addition polymerization of ethylene oxide with bisphenol represented by the following formula (II).

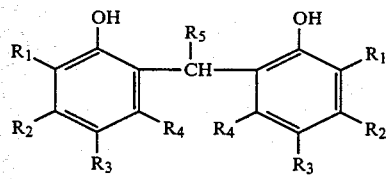

wherein $R_1$, $R_2$, $R_3$, $R_4$ and $R_5$ each represents the same meaning as described above.

Bisphenols represented by the formula (II) are synthesized by a process which comprises reacting a phenol derivative represented by the formula (III) with formaldehyde, acetaldehyde or furfural in the presence of an acid catalyst as described in, for example, *Journal of the American Chemical Society*, 74, 3410–3411 (1952), but they may be synthesized by other processes. The process for synthesizing them is not restricted.

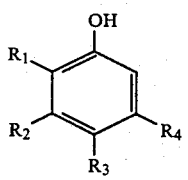

wherein $R_1$, $R_2$, $R_3$ and $R_4$ each represents the same meaning as described above.

The phenol-formaldehyde resin is a mixture of polymers having various degrees of polymerization as described in *Kagaku Daijiten*, edited by Kagaku Daijiten Editorial Committee, Vol. 7, pages 731–733 (Column of Phenol Resin) (published by Kyoritsu Shuppan Co., 1964), *Gosei Jushi Kagaku*, written by Minoru Imote, page 193 (published by Zoshindo, 1949) and *Phenol Resin*, written by Shinichi Murakami (published by Nikkan Kogyo Shinbunsha, 1961). Accordingly, the phenol-formaldehyde resin is an amorphous vitric substance with which it is very difficult to carry out a purification operation for removing phenol derivatives on an industrial scale. Thus, it is substantially impossible to obtain phenolformaldehyde resins containing no phenol derivative. On the other hand, bisphenol represented by the formula (II) having good quality which shows a sharp melting point or boiling point can be easily obtained by a conventional operation utilized in the chemical industries, such as recrystallization or distillation, because it is a single compound.

In order to derive compounds having two polyoxyethylene chains in the molecule represented by the formula (I) from bisphenol represented by the formula (II) synthesized as described above, addition polymerization of ethylene oxide is carried out. A commonly used process comprises blowing an ethylene oxide gas in the presence of a base such as sodium hydroxide or potassium hydroxide, etc., in the same manner as described in *Shin Kaimenkasseizai*, written by Hiroshi Horiguchi, pages 644–670 (published by Sankyo Shuppan Co., 1975).

Examples of nonionic surface active agents having two polyoxyethylene chains in the molecule of the present invention represented by the formula (I) are shown in the following.

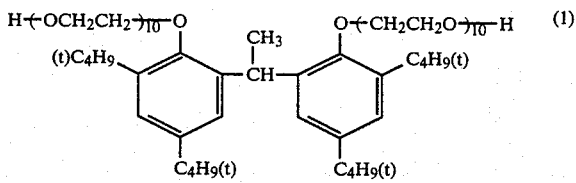

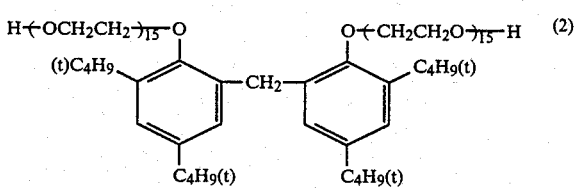

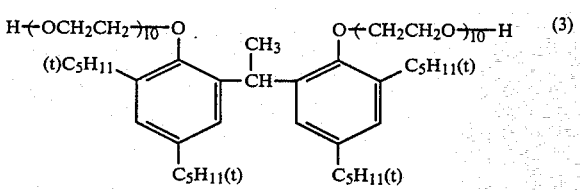

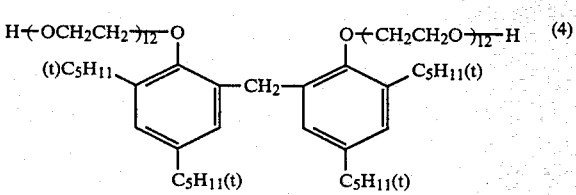

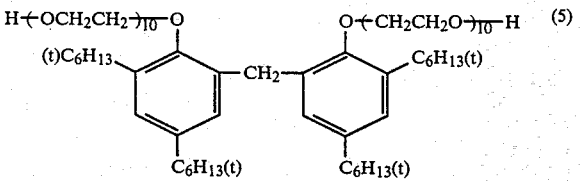

-continued

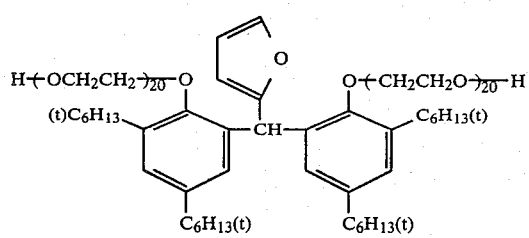
(6)

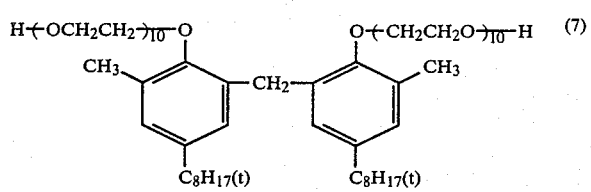
(7)

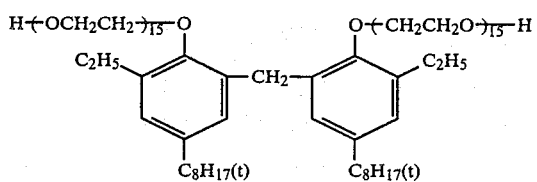
(8)

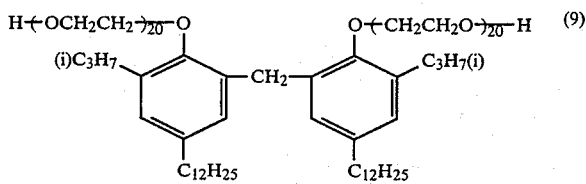
(9)

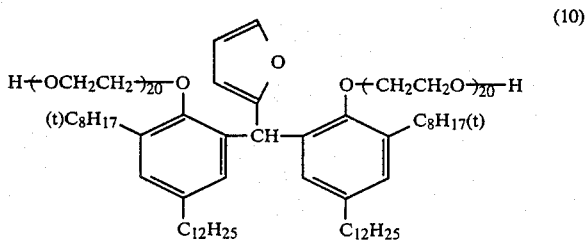
(10)

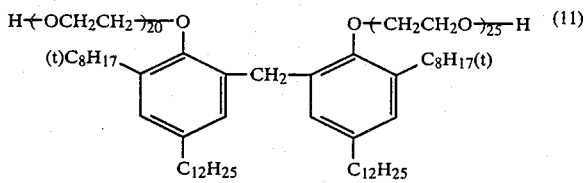
(11)

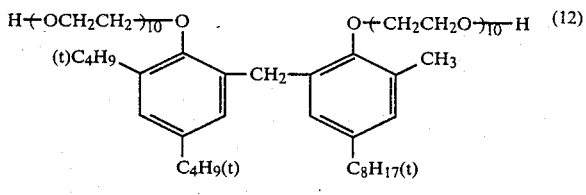
(12)

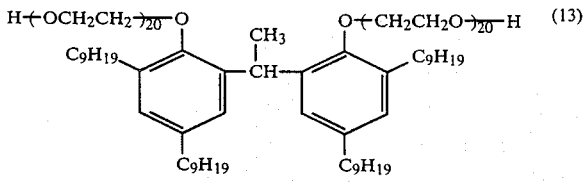
(13)

-continued

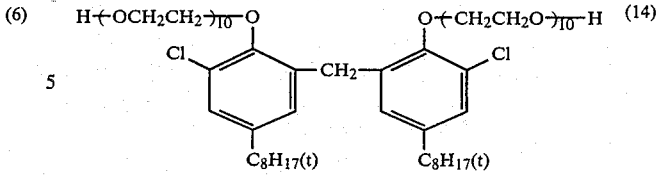
(14)

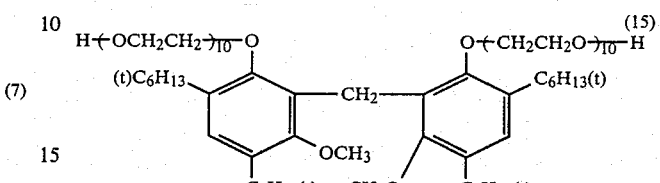
(15)

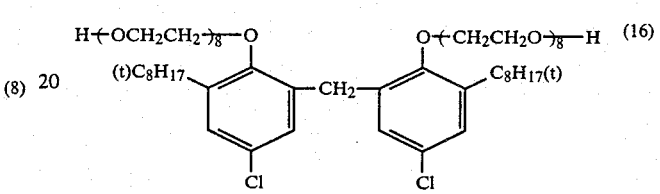
(16)

Preferred examples of nonionic surface active agents having two polyoxyethylene chains in the molecule of the present invention represented by the formula (I) include Compounds (1), (2), (3), (4), (5), (6), (10), (11), (15) and (16).

In the following, examples for synthesizing the nonionic surface active agents having two polyoxyethylene chains in the molecule of the present invention are described.

SYNTHESIS 1

Synthesis of Compound (7)

In a 200 ml three neck flask equipped with a stirrer and a reflux condenser, 44.1 g (0.2 mol) of 2-methyl-4-t-octylphenol, 3.9 g of paraformaldehyde, 1.9 g (0.01 mol) of p-toluenesulfonic acid monohydrate and 50 ml of glacial acetic acid were placed, and the mixture was heated to 50° C. with stirring. After being stirred for 5 hours with heating under the same condition as described above, the resulting solution was cooled to room temperature and poured into 300 ml of water with stirring to separate resinous precipitates. After the supernatant was removed, the precipitates were washed twice with water and thereafter recrystallized from 20 ml of acetonitrile to obtain 34.1 g of white crystals of bis(2-hydroxy-3-methyl-5-t-octylphenyl)-methane. Yield: 75%. Melting point: 98° to 99° C.

In a 200 ml three neck flask equipped with a stirrer and a reflux condenser, 22.6 g (0.05 mol) of bis(2-hydroxy-3-methyl-5-t-octylphenyl)methane synthesized as described above, 13 g of xylene and 0.3 g of potassium hydroxide were placed, and an ethylene oxide gas was bubbled into the mixture with stirring at 140° C. Stirring and heating were continued while bubbling the gas to polymerize ethylene oxide till the weight of the reacting solution increased 44 g (corresponding to 1 mol of ethylene oxide). After cooling to room temperature, 100 ml of methanol was added, and the mixture was neutralized with hydrochloric acid and subjected to decolorization treatment with decolorizing carbon. After the solvent was distilled off, 100 ml of ethyl acetate was added. After insoluble salts were removed by filtration, ethyl acetate was distilled off to obtain 62 g of light yellow waxy Compound (7).

SYNTHESIS 2

Synthesis of Compound (14)

34.6 g of white crystals of bis(2-hydroxy-3-chloro-5-t-octylphenyl)methane was obtained from 48.1 g (0.2 mol) of 2-chloro-4-t-octylphenol by the same method as in Synthesis 1. Yield: 70%. Melting point: 135° to 137° C.

44 g of ethylene oxide and 24.7 g (0.05 mol) of bis(2-hydroxy-3-chloro-5-t-octylphenyl)methane were subjected to addition polymerization by the same method as in Synthesis 1 to obtain 65 g of light yellow waxy Compound (14).

SYNTHESIS 3

Synthesis of Compound (3)

In a 200 ml of three neck flask equipped with a stirrer and a reflux condenser, 46.8 g (0.2 mol) of 2,4-di-t-amylphenol, 6.6 g of paraformaldehyde, 8 g (0.04 mol) of p-toluenesulfonic acid monohydrate and 50 ml of glacial acetic acid were placed, and the mixture was heated to 50° C. with stirring. After being stirred for 5 hours with heating under the same condition as described above, the resulting solution was cooled to room temperature and poured into 300 ml of water with stirring. The precipitates were separated by filtration. After being dried, they were recrystallized from about 50 ml of acetonitrile to obtain 29.6 g of white crystals of 1,1-bis(2-hydroxy-3,5-di-t-amylphenyl)ethane. Yield: 60%. Melting point: 111° to 113° C.

In a 200 ml three neck flask equipped with a stirrer and a reflux condenser, 24.8 g (0.05 mol) of 1,1-bis(2-hydroxy-3,5-di-t-amylphenyl)ethane synthesized as described above, 13 g of xylene and 0.3 g of potassium hydroxide were placed, and an ethylene oxide gas was bubbled into the mixture with stirring at 140° C. Stirring and heating were continued while bubbling the gas to polymerize ethylene oxide till the weight of the reacting solution increased 44 g (corresponding to 1 mol of ethylene oxide). After being cooled to room temperature, 100 ml of methanol was added, and the mixture was neutralized with hydrochloric acid and subjected to decolorization treatment with decolorizing carbon. After the solvent was distilled off, 100 ml of ethyl acetate was added. After insoluble salts were removed by filtration, ethyl acetate was distilled off to obtain 66 g of light yellow waxy Compound (3).

SYNTHESIS 4

Synthesis of Compound (1)

In a 500 ml three neck flask equipped with a stirrer, a reflux condenser and a water removal apparatus, 123.8 g (0.6 mol) of 2,4-di-t-butylphenol, 19.8 g of paraformaldehyde, 1.1 g (6 millimols) and 150 ml of toluene were placed, and the mixture was heated to 70° C. with stirring. Toluene was refluxed under a reduced pressure of 120 to 140 mm Hg and water formed with progress of the reaction was removed. Formation of water concluded after 2 hours from the start of the reaction. After then, toluene was distilled off under a reduced pressure, and the product was recrystallized from a mixed solvent composed of 500 ml of methanol and 75 ml of water to obtain 89 g of white crystals of 1,1-bis(2-hydroxy-3,5-di-t-butylphenyl)ethane. Yield: 68%. Melting point: 163° to 166° C.

Thereafter, addition polymerization of ethylene oxide was carried out in the same manner as in Synthesis 3 to obtain 58 g of light yellow waxy Compound (1) from 21.9 g of 1,1-bis(2-hydroxy-3,5-di-t-butylphenyl)ethane.

The amount of the nonionic surface active agent having two polyoxyethylene chains in the molecule of the present invention represented by the formula (I) varies according to the kind of the photographic material to be used or the coating process, etc., but it is generally 5 to 500 mg based on 1 $m^2$ of the photographic sensitive material. Particularly, an amount of 20 to 200 mg is preferred.

In order to apply the nonionic surface active agent having two polyoxyethylene chains in the molecule of the present invention represented by the formula (I) to layers in the photographic materials, it is dissolved in water or an organic solvent such as methanol, ethanol or acetone, etc., or a solvent mixture composed of water and said organic solvent. An amount of the nonionic surface active agent having two polyoxyethylene chains in the molecule of the present invention represented by the formula (I) based on the weight of water, an organic solvent or a solvent mixture thereof is preferably 1 to 30% by weight and particularly preferably 5 to 15% by weight. The resulting solution is then introduced into a light-sensitive emulsion layer or a light-insensitive auxiliary layer (for example, a backing layer, an antihalation layer, an intermediate layer or a protective layer, etc.) on the base or the solution is applied to the surface of the base by spraying, coating or dipping, followed by drying. In this case, two or more nonionic surface active agents having two polyoxyethylene chains in the molecule of the present invention may be used as a mixture.

Further, the nonionic surface active agent may be used together with a binder such as gelatin, polyvinyl alcohol, cellulose acetate, cellulose acetate phthalate, polyvinyl formal or polyvinyl butyral, etc., to form an antistatic layer.

In the layer containing the nonionic surface active agent having two polyoxyethylene chains in the molecule of the present invention represented by the formula (I) or other layers, other antistatic agents can be used together, by which a more suitable antistatic effect can be obtained. When the other antistatic agents are used together with the nonionic surface active agent having two polyoxyethylene chains in the molecule of the present invention represented by the formula (I), the amount of the other antistatic agents is preferably 1 to 5,000 mg, and particularly preferably 10 to 1,000 mg based on 1 $m^2$ of the photographic material. Examples of such antistatic agents include polymers described in U.S. Pat. Nos. 2,882,157, 2,972,535, 3,062,785, 3,262,807, 3,514,291, 3,615,531, 3,753,716, 3,938,999, 4,070,189 and 4,147,550, German Patent 2,800,466, and Japanese Patent Application (OPI) Nos. 91165/73, 94433/73, 46733/74, 54672/75, 94053/75 and 129520/77 (the term "OPI" as used herein refers to a "published unexamined Japanese patent application"), etc., surface active agents described in U.S. Pat. Nos. 2,982,651, 3,428,456, 3,457,076, 3,454,625, 3,552,978 and 3,655,387, etc., metal oxides and colloidal silica, etc., described in U.S. Pat. Nos. 3,062,700, 3,245,833 and 3,525,621, etc., and the so-called matting agents such as barium strontium sulfate, polymethyl methacrylate, methyl methacrylatemethacrylic acid copolymer, colloidal silica or powdery silica, etc.

Further, polyol compounds described in Japanese Patent Application (OPI) No. 89626/79 such as ethylene glycol, propylene glycol or 1,1,1-trimethylolpropane, etc., may be added to the layer containing the nonionic surface active agent having two polyoxyethylene chains in the molecule of the present invention represented by the formula (I) or other layers, by which a more suitable antistatic effect can be obtained. When the polyol compounds are used together with the nonionic surface active agent having two polyoxyethylene chains in the molecule of the present invention represented by the formula (I), the amount of the polyol compounds is preferably 5 to 5,000 mg, and particularly preferably 100 to 1,000 mg based on 1 m$^2$ of the photographic material.

The layer containing the nonionic surface active agent having two polyoxyethylene chains in the molecule of the present invention may be an emulsion layer, a subbing layer provided on the same side of the emulsion layer, an intermediate layer, a surface protective layer, an overcoat layer, a back layer provided on the reverse side of the emulsion layer, etc. Among them, surface layers such as the surface protective layer, the overcoat layer and the back layer, etc., are preferred.

Examples of the base capable of applying the nonionic surface active agent having two polyoxyethylene chains in the molecule of the present invention include films of polyolefin such as polyethylene, polystyrene, cellulose derivatives such as cellulose acetate and esters such as polyethylene terephthalate, etc., baryta paper, synthetic paper, and paper both sides of which are covered with the above-described polymer film, and analogous base. Preferred examples of the base capable of applying the nonionic surface active agent having two polyoxyethylene chains in the molecule of the present invention include films of cellulose acetate (particularly, cellulose triacetate) and polyethylene terephthalate.

An antihalation layer may be formed on the base used in the present invention. For this purpose, it is possible to use carbon black or various dyes, for example, oxonol dyes, azo dyes, arylidene dyes, styryl dyes, anthraquinone dyes, merocyanine dyes and tri-(or di-)arylmethane dyes, etc. Useful binders for the carbon black or dyes include cellulose acetate (di- or mono-), polyvinyl alcohol, polyvinyl butyral, polyvinyl acetal, polyvinyl formal, polymethacrylic acid ester, polyacrylic acid ester, polystyrene, styrene-maleic acid anhydride copolymer, polyvinyl acetate, vinyl acetate-maleic acid anhydride copolymer, methyl vinyl ether-maleic acid anhydride copolymer, polyvinylidene chloride and derivatives thereof.

Photographic materials used in connection with the present invention include conventional black-and-white silver halide photographic materials (for example, black-and-white photographic materials for photographing, black-and-white photographic materials for X-rays and black-and-white photographic materials for printing, etc.), conventional multilayer color photographic materials (for example, color reversal films, color negative films and color positive films, etc.) and various photographic materials. Particularly, the effect of the present invention is great in case of silver halide photographic materials for high speed processing at a high temperature and silver halide photographic materials having high sensitivity.

In the following, photographic layers in the silver halide photographic materials according to the present invention are illustrated in brief.

Useful binders for the photographic layers include proteins such as gelatin or casein, etc., cellulose compounds such as carboxymethyl cellulose or hydroxyethyl cellulose, etc., saccharose derivatives such as agar, sodium alginate or starch derivatives, etc., synthetic hydrophilic colloids such as polyvinyl alcohol, poly-N-vinylpyrrolidone, polyacrylic acid, polyacrylamide or derivatives thereof or partially hydrolyzed products thereof.

Gelatin used here means the so-called lime-processed gelatin, acid-processed gelatin and enzyme-processed gelatin.

A part or all of the gelatin can be replaced by synthetic high molecular substances. Further, it may be replaced by the so-called gelatin derivatives, namely, those which are prepared by modifying functional groups in the molecule such as amino groups, imino groups, hydroxy groups or carboxyl groups with a reagent having a group capable of reacting with them, or graft polymers of gelatin wherein molecular chains of high polymers are bonded thereto.

The kind of silver halide, the process for production thereof, the method of chemical sensitization, antifogging agents stabilizers, hardeners, antistatic agents, plasticizers, lubricants, coating assistants, matting agents, whitening agents, spectrally sensitizing dyes, dyes and color couplers, etc., used in silver halide emulsion layers and the surface protective layers, etc., in the photographic materials of the present invention are not particularly restricted, which can be referred to the description of, for example, *Product Licensing,* Vol. 92, pages 107–110 (December 1971) and *Research Disclosure,* Vol. 176, pages 22–31 (December 1978).

Useful antifogging agents and stabilizers include compounds such as heterocyclic compounds including 4-hydroxy-6-methyl-1,3,3a,7-tetraazaindene-3-methylbenzothiazole and 1-phenyl-5-mercaptotetrazole, mercury containing compounds, mercapto compounds or metal salts, etc. Examples of hardeners include aldehyde compounds such as mucochloric acid, mucobromic acid, mucophenoxychloric acid, mucophenoxybromic acid, formaldehyde, dimethylol urea, trimethylol melamine, glyoxal, monomethyl glyoxal, 2,3-dihydroxy-1,4-dioxane, 2,3-dihydroxy-5-methyl-1,4-dioxane, succinaldehyde, 2,5-dimethoxytetrahydrofuran or glutaraldehyde, active vinyl compounds such as divinyl sulfone, methylenebismaleimide, 5-acetyl-1,3-diacryloyl-hexahydro-s-triazine, 1,3,5-triacryloylhexahydro-s-triazine, 1,3,5-trivinylsulfonyl-hexahydro-s-triazine-bis(vinylsulfonylmethyl)ether, 1,3-bis(vinylsulfonylmethyl)propanol-2 or bis($\alpha$-vinylsulfonylacetamido)ethane, active halogen compounds such as 2,4-dichloro-6-hydroxy-s-triazine.sodium salt, 2,4-dichloro-6-methoxy-s-triazine, 2,4-dichloro-6-(4-sulfoanilino)-s-triazine.sodium salt, 2,4-dichloro-6-(2-sulfoethylamino)-s-triazine or N,N'-bis(2-chloroethylcarbamoyl)piperazine, epoxy compounds such as bis(2,3-epoxypropyl)-methylpropyl ammonium.p-toluenesulfonate, 1,4-bis(2',3'-epoxypropyloxy)butane, 1,3,5-triglycidylisocyanurate or 1,3-diglycidyl-5-($\gamma$-acetoxy-$\beta$-oxypropyl)isocyanurate, ethyleneimine compounds such as 2,4,6-ethyleneimino-s-triazine, 1,6-hexamethylene-N,N'-bisethylene urea or bis-$\beta$-ethyleneiminoethyl thioether, methanesulfonic acid esters such as 1,2-di(methanesulfonyloxy)ethane, 1,4-di(methanesulfonyloxy)- butane or 1,5-di(methanesulfonyloxy)-pentane, carbodiimide compounds, isoxazole compounds, and inorganic compounds such as chromium alum.

Known surface active agents may be added to the photographic layers in the present invention. Examples of useful surface active agents include natural surface active agents such as saponin, etc., nonionic surface active agents such as glycerin type agents or glycidol type agents, cationic surface active agents such as higher alkylamines, quaternary ammonium salts, pyridine and other heterocyclic derivatives, phosphonium or sulfonium compounds, etc., anionic surface active agents containing acid groups such as carboxylic acids, sulfonic acids, phosphoric acids, sulfuric acid esters or phosphoric acid esters, etc., and ampholytic surface active agents such as amino acids, aminosulfonic acids, or sulfuric or phosphoric acid esters of aminoalcohols, etc. Further, fluorine containing surface active agents can be used together.

Further, the photographic materials of the present invention may contain alkyl acrylate type latexes described in U.S. Pat. Nos. 3,411,911 and 3,411,912 and Japanese Patent Publication No. 5331/70 in the photographic layers.

In the following the present invention is illustrated with reference to the following example, but the present invention is not limited to the example.

EXAMPLE (1) Preparation of Samples

To a polyethylene terephthalate film base having a thickness of 180$\mu$ which was subjected to undercoating, a silver halide emulsion layer having the following composition was applied and a protective layer having the following composition was applied to said layer and dried to prepare black-and-white silver halide photographic materials. To the protective layer, a nonionic surface active agent of the present invention or a surface active agent for comparison was added.

Emulsion Layer

Thickness: about 5$\mu$
Composition and coating amount:
Gelatin—2.5 g/m$^2$
Silver iodobromide (silver iodide: 1.5% by mol)—5 g/m$^2$
1-Phenyl-5-mercaptotetrazole—25 mg/m$^2$ Protective Layer Thickness: about 1$\mu$
Composition and coating amount:
Gelatin—1.7 g/m$^2$
2,6-Dichloro-6-hydroxy-1,3,5-triazine sodium salt—10 mg/m$^2$
Sodium dodecylsulfate—10 mg/m$^2$
Nonionic surface active agent of the present invention or nonionic surface active agent for comparison—60 mg/m$^2$ (2) Method of Determining Antistatic Property The antistatic property was determined by measuring surface resistivity and generation of static marks. (1) Measurement of the surface resistivity was carried out by putting a test strip of the sample between brass electrodes (using stainless steel in the part contacting with the test strip) having a length of 10 cm with a space between electrodes of 0.14 cm and measuring a 1 minute value by means of an insulation tester: Type TR 8651 produced by Takeda Riken Co. (2) The static mark generation test was carried out by a method which comprises putting an unexposed photographic material on a rubber sheet so that the surface containing the antistatic agent faced to the rubber sheet, pressing the photographic material by a rubber roll, and separating it to generate static marks.

The surface resistivity was measured at 25° C. and 25% RH and the static mark generation test was carried out at 25° C. and 25% RH. Conditioning of the test strips of the sample was carried out under the above-described condition for a whole day and night.

In order to evaluate the degree of generation of static mark, each sample was developed at 20° C. for 5 minutes with a developing solution having the following composition.

Composition of Developing Solution

N-Methyl-p-aminophenol sulfate—4 g
Anhydrous sodium sulfite—60 g
Hydroquinone—10 g
Sodium carbonate (monohydrate)—53 g
Potassium bromide—25 g
Water to make—1 liter Evaluation of the static mark was carried out according to the following standard consisting of 5 stages classified with respect to the rate of area of portions exposed with electric discharge.

A: less than 1%
B: from 1 to 10%
C: from 11 to 30%
D: from 31 to 50%
E: more than 50%

(3) Method of Testing Deterioration with the Passage of Time

After the above-described samples and high quality white paper were conditioned at 25° C. and 70% RH for 1 hour, the high quality paper was put between two samples so that both sides of the high quality paper came into contact with the surface of the emulsion layer side of the samples, and they were put in a polyethylene laminated bag and sealed. These samples were allowed to stand at room temperature for a week while applying a weight of 40 g/cm$^2$. Thereafter, the antistatic property was measured according to the above-described method of determining antistatic property and it was compared with that before the passage of time.

(4) Method of Testing Photographic Properties

After the above-described sample was exposed to light by a tungsten lamp through a filter: SP-14 produced by Fuji Photo Film Co., it was developed with a developing solution having the following composition (at 35° C. for 30 seconds), fixed and washed. Then, photographic properties were examined.

Composition of Developing Solution

Hot water—800 ml
Sodium tetrapolyphosphate—2.0 g
Anhydrous sodium sulfate—50 g
Hydroquinone—10 g
Potassium carbonate (monohydrate)—40 g
1-Phenyl-3-pyrazolidone—0.3 g
Potassium bromide—2.0 g
Water to make—1,000 ml

(5) Measurement of Degree of Screen Contamination

Test strips and a screen: LT-II produced by Dainippon Toryo Co. were conditioned at 30° C. and 80% RH for 1 day. After 100 test strips were allowed to pass in a cassette using LT-II under the same condition, photographing was carried out with X-rays and the degree of uneven density was examined.

Evaluation of the degree of screen contamination was carried out according to the following standard consisting of 4 stages.

A: Generation of uneven density was not observed.
B: Uneven density was slightly generated.
C: Uneven density was considerably generated.
D: Uneven density was remarkably generated.

Results of each test (2) to (5) are shown in Table 1.

However, with Comparative Compounds A and B which have one polyoxyethylene chain in the molecule, the antistatic property before the passage of time is excellent, but it deteriorates with the passage of time. Further, they remarkably deteriorate the photographic sensitivity and the screen contamination property.

Further, with Comparative Compound C which is an ethylene oxide addition polymer of phenol-formaldehyde resin, it is inevitable that the antistatic property deteriorates with the passage of time, the photographic sensitivity reduces and the screen contamination property deteriorates.

Furthermore, when Compound (3) having two polyoxyethylene chains in the molecule of the present invention is used together with Comparative Compound B having one polyoxyethylene chain in the molecule as a

TABLE 1

| | | Antistatic Property | | | | | |
|---|---|---|---|---|---|---|---|
| | | Before Passage of Time | | After Passage of Time | | Photographic | |
| Sample No. | Antistatic Agent | Surface Resistivity ($\Omega$) | Static Mark | Surface Resistivity ($\Omega$) | Static Mark | Sensitivity (relative value) | Degree of Screen Contamination |
| 1 | Compound (1) of the present invention | $2.0 \times 10^{11}$ | A | $3.1 \times 10^{11}$ | A | 96 | A |
| 2 | Compound (3) of the present invention | $2.7 \times 10^{11}$ | A | $2.5 \times 10^{11}$ | A | 100 | A |
| 3 | Compound (4) of the present invention | $4.1 \times 10^{11}$ | A | $4.2 \times 10^{11}$ | A | 99 | A |
| 4 | Compound (5) of the present invention | $6.0 \times 10^{11}$ | A | $5.2 \times 10^{11}$ | A | 98 | A |
| 5 | Compound (7) of the present invention | $2.5 \times 10^{11}$ | A | $3.7 \times 10^{11}$ | A | 96 | A |
| 6 | Compound (9) of the present invention | $3.3 \times 10^{11}$ | A | $2.2 \times 10^{11}$ | A | 98 | A |
| 7 | Compound (10) of the present invention | $4.5 \times 10^{11}$ | A | $3.9 \times 10^{11}$ | A | 97 | A |
| 8 | Compound (14) of the present invention | $3.0 \times 10^{11}$ | A | $3.8 \times 10^{11}$ | A | 96 | A |
| 9 | Comparative Compound A | $2.3 \times 10^{11}$ | A | $8.7 \times 10^{13}$ | D | 78 | D |
| 10 | Comparative Compound B | $3.0 \times 10^{11}$ | A | $8.1 \times 10^{13}$ | D | 73 | D |
| 11 | Comparative Compound C | $4.8 \times 10^{11}$ | A | $7.9 \times 10^{12}$ | C | 86 | C |
| 12 | Mixture of Compound (3) of the present invention and Comparative Compound B (mixing ratio, 2:1) | $2.9 \times 10^{11}$ | A | $7.0 \times 10^{12}$ | C | 85 | C |
| 13 | Blank | $5.9 \times 10^{14}$ | E | $7.6 \times 10^{14}$ | E | 100 | A |

Comparative Compound A
$(n)C_{12}H_{25}O\text{-}(CH_2CH_2O)_{\overline{10}}\text{-}H$
(British Patent 861,134)

Comparative Compound B

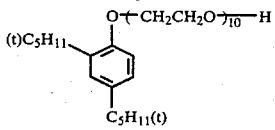

Comparative Compound C

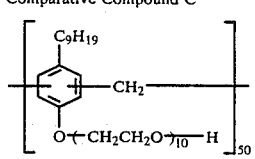

(U.S. Pat. No. 3,850,641, Compound I-3)

Table 1 clearly shows that photographic materials containing the compound having two polyoxyethylene chains in the molecule of the present invention have a sufficiently low surface resistivity and almost no static marks. Table 1 also shows that the photographic sensitivities of such materials are hardly reduced, and the screen contamination property is excellent. Further, this excellent antistatic property hardly changes with the passage of time.

mixture, it is observed that the antistatic property deteriorates with the passage of time, the photographic sensitivity reduces and the screen contamination property deteriorates.

Thus, it is understood that compounds having one polyoxyethylene chain in the molecule cause remarkable deterioration of properties, when they are used alone or as a mixture, and that compounds of the present invention which can be synthesized without containing compounds having one polyoxyethylene chain in the molecule show excellent properties which cannot be attained in ethylene oxide addition polymers of phenolformaldehyde resin.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising:
    a support base;
    a silver halide emulsion layer; and
    an antistatic layer containing a nonionic surface active agent having two polyoxyethylene chains in a molecule represented by the general formula (I):

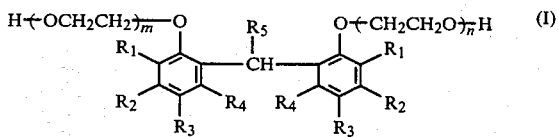

wherein $R_1$ and $R_3$ each represents a substituted or unsubstituted alkyl group, an aryl group, an alkoxy group, a halogen atom, an acyl group, an amido group, a sulfonamido group, a carbamoyl group or a sulfamoyl group, $R_2$ and $R_4$ each represents a hydrogen atom, a substituted or unsubstituted alkyl group, an aryl group, an alkoxy group, a halogen atom, an acyl group, an amido group, a sulfonamido group, a carbamoyl group or a sulfamoyl group, $R_5$ represents a hydrogen atom, a methyl group or an α-furyl group, and m and n independently represents an average degree of polymerization of ethylene oxide, which is 55 to 30, wherein the compound represented by the formula (I) is present in an amount within the range of 20 to 200 mg/m² of the support base.

2. A silver halide photograhic light-sensitive material as claimed in claim 1, wherein the antistatic layer is the outermost layer of the photographic material.

3. A silver halide photographic light-sensitive material as claimed in claim 2, wherein the outermost layer is a protective layer.

4. A silver halide photographic light-sensitive sensitive material as claimed in claim 1, wherein $R_1$ and $R_3$ each represents an alkyl group.

5. A silver halide photographic light-sensitive material as claimed in claim 1, wherein $R_2$ and $R_4$ each represents a hydrogen atom.

6. A silver halide photographic light-sensitive material as claimed in claim 1, wherein $R_5$ is a methyl group or an α-furyl group.

7. A silver halide photographic light-sensitive material as claimed in claim 1, wherein $R_1$ is a bulky tertiary alkyl group.

8. A silver halide photographic light-sensitive material as claimed in claim 7, wherein $R_1$ is a t-butyl group, a t-amyl group or a t-octyl group.

* * * * *